United States Patent [19]

Steigelmann et al.

[11] 4,239,506

[45] Dec. 16, 1980

[54] USE OF AQUEOUS, NON-SWEEP LIQUID DURING MEMBRANE SEPARATION

[75] Inventors: Edward F. Steigelmann; Robert D. Hughes, both of Naperville, Ill.

[73] Assignee: Standard Oil Company (Indiana), Chicago, Ill.

[21] Appl. No.: 703,942

[22] Filed: Jul. 9, 1976

Related U.S. Application Data

[63] Continuation of Ser. No. 498,112, Aug. 16, 1974, abandoned.

[51] Int. Cl.³ .............................................. B01D 59/10
[52] U.S. Cl. ........................................ 55/16; 210/651
[58] Field of Search ............... 210/23 F, 23 H; 55/16, 55/158

[56] References Cited

U.S. PATENT DOCUMENTS

| | | | |
|---|---|---|---|
| 3,758,603 | 5/1973 | Steigelmann et al. | 55/16 |
| 3,812,651 | 9/1973 | Steigelmann | 55/16 |

*Primary Examiner*—Ernest G. Therkorn
*Attorney, Agent, or Firm*—Bernard & Brown

[57] ABSTRACT

A material is separated from a fluid mixture by contacting the mixture containing the material with a first side of essentially solid, water-insoluble, hydrophilic, semi-permeable membrane in contact with an aqueous liquid barrier having ions which combine with the material to be separated to form a water-soluble complex. The partial pressure of the material on a second side of the semi-permeable membrane is sufficiently less than the partial pressure of the material in the mixture to provide separated material on the second side of the membrane. The separated material can be removed from the vicinity of the second side of the membrane by a gas stream. The second side of the membrane is contacted with an aqueous liquid medium to reduce the loss of the aqueous liquid barrier from the membrane which may otherwise decrease in separation efficiency during use due to water losses. The gas stream used to remove the separated material may be supersaturated with the aqueous medium, e.g. water, and may contact the membrane with the aqueous medium via condensation. Alternatively, the aqueous medium such as water may be applied by a continuous or intermittent film, spray or mist. The process is particularly useful for separating olefins, especially ethylene.

19 Claims, No Drawings

USE OF AQUEOUS, NON-SWEEP LIQUID DURING MEMBRANE SEPARATION

This is a continuation of application Ser. No. 498,112, filed Aug. 16, 1974, now abandoned.

This invention relates to an improved process for separating a material from a fluid mixture containing it by utilizing metal-complexing techniques employing an essentially solid, water-insoluble, hydrophilic, semi-permeable membrane in contact with an aqueous liquid barrier containing ions which combine with the material to be separated to form a water-soluble complex. In the process the loss of water from the membrane is materially reduced by contacting the surface of the membrane from which the separated material leaves the membrane, i.e., the exit surface, with an aqueous liquid medium while the separation proceeds. The separated material can be removed from the vicinity of the exit surface of the membrane by, for example, a sweep gas stream.

There is considerable commercial interest in separating components, e.g., aliphatically-unsaturated hydrocarbons, from mixtures containing such materials. These aliphatically-unsaturated hydrocarbons are reactive materials that serve in various roles in chemical syntheses. A number of the unsaturated hydrocarbons are employed as monomers in the formation of polymers and, in this regard, olefins such as ethylene, propylene, butadiene and isoprene are well known. These olefins, as well as other unsaturated materials, for instance, acetylene, are also used to form relatively low molecular weight products.

The aliphatically-unsaturated hydrocarbons are most often made available on a commerical basis in admixture with other chemical compounds, frequently other hydrocarbons. These unsaturated hydrocarbon-containing streams are usually by-products of chemical syntheses or separation processes. When the hydrocarbon streams are liquid under normal conditions or can readily be made so, ordinary distillation techniques can be used to separate the hydrocarbon components, providing they have sufficiently different boiling points for the process to be economically feasible. Especially when the hydrocarbon mixtures contain materials having close boiling points, which is frequently the case with hydrocarbons of the same number of carbon atoms or having a difference of only one carbon atom, distillation may not be an attractive separation procedure. In such cases, more expensive processes are often used and involve operations such as solvent extraction or extractive distillation which entail considerable expense, if indeed they are technically feasible in a given situation.

When the mixture containing the aliphatically-unsaturated hydrocarbon is essentially in a gaseous state at normal or ambient conditions of temperature and pressure, separation of the desired component from the mixture may be even more troublesome. In these situations, cryogenic processes may be used, but they are expensive. The components of these normally gaseous mixtures may not even have particularly close boiling points, but, nevertheless, the mixture must be cooled in order to separate one or more of its components. In spite of the considerable cost of cryogenic operations, the procedure has been employed commercially for the separation of ethylene from other gaseous materials such as ethane and methane.

Several of our patents and pending patent applications described methods for separating materials such as aliphatically-unsaturated hydrocarbons and carbon monoxide, from mixtures containing them, and these procedures involve the combined use of liquid barrier permeation and metal-complexing techniques which can exhibit high selectivity factors. In the processes, the liquid barrier is an aqueous solution having metal-containing ions which will complex with the material to be separated, and the liquid barrier is employed in conjunction with a semi-permeable membrane which is essentially impermeable to the passage of liquid. In several systems of this type, the liquid barrier containing the complex-forming ions is in contact with the membrane and preferably is at least partially contained in a hydrophilic, semi-permeable film membrane. When operating in this preferred manner, it is not necessary to maintain contact of the film with a separate or contiguous aqueous, complex-forming, liquid phase during the process, and this may facilitate the use of a greater variety of semi-permeable members as far as physical configuration is concerned. Thus, the membranes can be designed without having to provide a separate liquid phase adjacent the inlet side of the membrane film, and this may enable the use of membrane configurations having a greater surface or contact area. Such a separate liquid phase may, however, be employed. The film membranes can be essentially homogenous materials which are suitable for forming into various shapes, and the membranes may be formed by, for instance, extrusion and can be made into hollow fiber forms. These fibers are preferred membrane configurations because they have the advantages of high surface area per unit volume, thin walls for high transport rates, and high strength to withstand substantial pressure differentials across the membrane or fiber walls.

This invention is directed to an improved process of these types in which a material is separated from a fluid mixture by utilizing an essentially solid, water-insoluble, hydrophilic, semi-permeable membrane having therein an aqueous liquid barrier containing ions which combine with the material to be separated to form a water-soluble complex, and during the separation, an aqueous liquid medium, i.e., an aqueous, non-sweep liquid medium, e.g. water in the liquid phase, with or without other constituents, is provided on the exit surface of the membrane from a source extraneous to the membrane to decrease water loss from the film and thereby enhance the operation of the separation system. In the process a material is separated from a feed mixture by contacting the latter with a first side of the membrane while having a partial pressure of the material on a second or exit side of the semi-permeable membrane which is sufficiently less than the partial pressure of the material in the mixture to provide separated material on the second side of the membrane. The separated material can be removed from the vicinity of the second side of the membrane by, for instance, a sweep gas. By the process of this invention, the loss of water from aqueous liquid barrier in the membrane is materially reduced and decreases in permeability and selectivity during operation are thereby minimized. Similar results were not obtained when the feed mixtures and sweep gas are merely saturated with moisture.

Typically the amount of the aqueous liquid medium contacted with the surface of the membrane from its exit side as the separation proceeds is sufficient to retard water loss from the membrane. Such amounts may vary depending upon the type of membrane and operating conditions, and generally sufficient of the aqueous liquid medium is supplied to retard or prevent crystallization of the metal-containing ionic component from the liquid barrier solution. In one preferred embodiment of this invention, a supersaturated gas stream is used to remove the separated material from the exit side of the membrane, and water is deposited onto the exit side of the membrane by condensation from the supersaturated gas stream. The supersaturated sweep gas flow rate may be chosen to adequately remove the separated material from the vicinity of the exit or discharge side of the membrane, and the extent of supersaturation may be determined based on water losses and on the chosen sweep gas flow rate. Suitable temperatures for the sweep gas may be about 40° to 120° F., preferably about 70° to 110° F. It is preferred that sufficient aqueous medium be contacted with the exit side of the membrane to maintain the water content of the membrane substantially constant during the separation and to thus maintain a substantially constant concentration of complexing ions in solution during the separation.

The supersaturated sweep gas stream is preferably a gas which is relatively inert to reaction with the material separated, and the gas may be supersaturated by any suitable means. For example, the gas may be heated, saturated with water and then appropriately cooled to create a supersaturated gas. Other supersaturation techniques may be used such as pressure change supersaturation methods. Various methods may be used to contact the water-containing gas stream with the discharge side of the membrane employed in the separation process at the desired temperature, flow, and supersaturation conditions.

In a preferred embodiment of this invention, the aqueous medium contacts the exit side of the membrane by liquid aqueous medium discharge. For example, sprays, mists, flowing streams, films, or other liquid forms can be employed near or at the membrane exit side to permit liquid discharge onto the exit side of the membrane. The water discharge rate should be sufficient to adequately decrease aqueous liquid barrier losses from the membrane and may be continuous or intermittent. For example, a fine mist of aqueous medium may be continuously directed onto the exit side of the membrane or an intermittent stream may be discharged whenever, for instance, separation selectivity or permeability drops below a desired value. These processes may include automatic control which measures selectivity or permeability and is set to initiate a discharge of a predetermined quantity of aqueous medium whenever the measured condition drops below a predetermined level. Alternatively, intermittent discharge may be based on a predetermined or set frequency or time period.

Whenever the membrane is contacted with the aqueous medium by direct liquid discharge, it is desirable to substantially saturate or humidify the sweep gas stream to avoid having the sweep gas capture the deposited moisture. However, this substantial saturation or humidification of sweep gas may be accomplished in the vicinity of the membrane as, for example, simply by including sufficient aqueous medium in the spray or other discharge means so as to substantially saturate or humidify the sweep gas. The aqueous medium is essentially water but may include other components such as complexing ion components, e.g. silver nitrate. Additionally, the aqueous medium may contain other separation enhancing components such as, for example, hydrogen peroxide, as more fully described in commonly-assigned copening application, Ser. No. 512,972, filed on Oct. 7, 1974, now U.S. Pat. No. 4,014,665.

In another embodiment of the present invention, a vacuum is used to remove the separated material. In this embodiment the aqueous medium can be deposited by liquid discharge means, as discussed above. The vacuum is maintained so as to adequately remove the separated material, but is not so great as to have an undue detrimental effect on the aqueous medium contact to the membrane surface. Generally, a vacuum may be used to adequately remove the separated material, but to avoid aqueous medium losses by suction. The vacuum pressure is chosen such that the partial pressure of the material to be separated on the low pressure side of the membrane, i.e., the exit side, is less than that of the material to be separated on the high pressure or inlet side.

In one preferred embodiment of the present invention, the exit side of the membrane surface is contacted with a continuous liquid phase film of the aqueous medium, i.e., the exit side surface is kept substantially completely wetted. This may be accomplished by either continuous or intermittent delivery of aqueous medium to the continuous liquid phase film by various of the above-mentioned techniques. In the system in which hollow fibers are used as the membranes, the continuous liquid phase aqueous medium film may be advantageously used when the feed to be separated is passed through the inside of the fibers and the separated material exits from the outside of the fibers. When the continuous liquid phase aqueous medium film is employed, the separated material may be removed from the exit side of the membrane by, for instance, bubbling sweep gas through the liquid phase aqueous medium film.

The membranes employed in the process of the present invention are hydrophilic at least to some extent and include those membranes which contain additional hydrophilic and/or hygroscopic agents, and those that do not. A film membrane may be considered hydrophilic if it absorbs at least about 5 weight percent of water when immersed in distilled water for one day at room temperature and pressure. Typical membranes are those formed of film-forming materials such as nylon, e.g., the N-alkoxyalkyl polyamides, and those formed of nylon and more hydrophilic polymers such as polyvinyl alcohol, polyvinyl ethers, polyacrylamides and the like. The membrane materials may be formed into single membrane structures of desired configuration, as for example, by casting, or they may be formed into hollow fibers by hot melt extrusion and subsequently "bundled" into an array with potting compounds. The hollow fiber membranes are preferred because they provide the greatest surface contact area, and when the feed gas passes through the inside of the fibers, the cylindrical configuration provides a greater surface area on the exit side than on the inlet side which may promote separated gas transfer to the exit side. Additionally, surprisingly exceptional separation is achieved with the hollow fiber membranes when the feed gas is passed to the outside of the fibers and the sweep gas is passed through the inside of the fibers and the separated material passes from the outside to the inside of the hollow fibers, particularly when the outside of the fibers is flooded with the liquid barrier solution.

Regardless of the particular membrane configuration employed in the process of this invention, it is desirable to arrange the membrane so as to avoid uneven distribution of the contacting aqueous medium by gravity. In processes in which a flat membrane is essentially vertically positioned, it is preferable to contact the exit side of the membrane with the aqueous medium at its highest point so that gravity will favorably distribute the aqueous medium over the surface of the exit side. The vertical flat membrane may be tilted so as to assure that the aqueous medium "flows" into the membrane. Alternatively, the flat membrane may advantageously be placed in a horizontal position with the exit side facing upwardly. When fibers are used as the membrane and are situated to run generally horizontal they may be tilted with the segment which is first contacted with the aqueous medium as the higher end to assure that it runs down the length of the outside of the fibers. This may also be achieved by arranging the fibers in a vertically mounted position.

In the separation process the liquid barrier contains a metal component which provides ions capable of forming a complex with the materials desired to be separated from a mixture. The source of the ions may be added to the film or be mixed with the polymer or film-forming constituents prior to formation of the film. The complex-forming component may be impregnated into the film in an aqueous or other form and when impregnated in aqueous form may or may not contain water in an amount sufficient to establish the aqueous liquid barrier used in the separation process. In any event, the membrane has sufficient water to form the aqueous liquid barrier when used in the separation process.

The amount of water in the liquid barrier employed may be a minor portion of the liquid phase, but preferably is a major portion or even substantially all of the liquid, on a metal compound-free basis. Thus, small or minor amounts of water, say as little as about 5 weight percent, on a compound-free basis in the liquid phase may serve to provide significant transport across the liquid barrier of the material to be separated. Any other liquid present in the barrier is preferably water-miscible and should be chosen as not to have a substantial deleterious effect on the separation to be accomplished. The liquid barrier may also contain a hygroscopic agent, e.g., in a minor amount, to improve the wetting or hydrophilic properties of the liquid and provide better contact with the feed gas.

The membrane containing the complex-forming metal may be handled and transported in an essentially non-aqueous form or with some water therein, for instance, an insufficient amount of water to be effecitve in the separation. In such case, water would be added to the membrane to give a film bearing sufficient water to be useful in performing the separation process. However, the membrane may tend to dry during use even when the membrane contains major amounts of hydrophilic polymers. This drying generally results in a considerable decrease in permeability and in selectivity for the separation and is counteracted by the process of this invention.

The process of the present invention may be employed to separate, for instance, one or more unsaturated hydrocarbons by the liquid barrier-complex-forming technique in which the barrier is at least partly contained in the membrane. Although the separated products provided may be quite pure materials, for instance, of greater than 99% purity, the separation procedure may be used merely to provide significant increase in the concentration of a given material in a mixture with other components of the feedstock.

The process can be employed to separate various materials from other ingredients of the feed mixture providing at least one of the materials exhibits a complexing rate or transfer rate across the liquid barrier that is greater than at least one other dissimilar or different component of the feedstock. Quite advantageously, the system can be used to separate aliphatically-unsaturated hydrocarbons from other hydrocarbons which may be aliphatically-saturated or aliphatically-unsaturated, or from non-hydrocarbon materials, including fixed gases such as hydrogen. The feed mixture may thus contain one or more paraffins, including cycloparaffins, mono- or polyolefins, which may be cyclic or acyclic, and acetylenes or alkynes, and the mixture may include aromatics having such aliphatic configurations in a portion of their structure. often, the feed mixture contains one or more other hydrocarbons having the same number of carbon atoms as the unsaturated hydrocarbon to be separated or only a one carbon atom difference. Among the materials which may be separated according to this invention are ethylene, propylene, butenes, butadiene, isoprene, acetylene and the like.

In the method, the mixture containing the material to be separated may be essentially in the gaseous or vapor phase when in contact with the liquid barrier having dissolved therein one or more metal-containing ions which form a complex with the material to be separated. The liquid barrier can be essentially entirely within the semi-permeable membrane which may be permeable to the mixture in the absence of the liquid barrier. The membrane can be said to somewhat immobilize the liquid barrier within the membrane and the membrane in the presence of the liquid barrier is selective to the passage of the component of the feedstock to be separated. Since there is little, if any, passage for the feedstock across the separation zone except by becoming part of or reacting with the liquid barrier, this liquid barrier controls the selectivity of the liquid barrier-semi-permeable membrane combination. Since the water content of the liquid barrier is maintained at a desired operating level in the process of this invention, high selectivity and permeability are thereby assured.

The liquid barrier contains sufficient water and soluble metal-containing ions to form a suitable complex with at least one component of the feed subjected to the separation procedure. The metal ions form the complex upon contact with the feed, and, in addition, the complex dissociates back to the metal-containing ion and a component of the complex which was in the feed, under the conditions which exist on the discharge side of the liquid barrier and semi-permeable membrane as employed in the process. The released feed component exits the discharge side of the membrane and can be removed from the vicinity of the barrier and its supporting structure as by a sweep gas or through the effect of vacuum on this side of the barrier as discussed above. Thus the metal complex forms and is decomposed in the complex metal ion-containing liquid barrier, and, as a result, the material passing through the barrier is more concentrated with respect to at least one component present in the feed stream.

Often, the reactivity of aliphatically-unsaturated hydrocarbons with the complexing metal ions in their order of decreasing activity goes from acetylenes or dienes to monoolefins, the aliphatically-saturated hydrocarbons and other materials present being essentially non-reactive. Also, different reactivities may be exhibited among the various members of a given type of aliphatically-unsaturated hydrocarbon. The process can thus be used to separate paraffins from monoolefins, diolefins or acetylenes; diolefins from monoolefins; or acetylenes from paraffins, monoolefins or diolefins; as well as to separate a given aliphatically-unsaturated hydrocarbon from another of such materials in its class where the members have differing complexing rates with or transport rates across the liquid barrier. The feed need only contain a small amount of aliphatically-unsaturated hydrocarbon, as long as the amount is sufficient so that the unsaturated material to be separated selectively reacts with the metal-containing ions to a significant extent, and thus at least one other component of the feed is less reactive or non-reactive with the complex-forming metal ions.

The aliphatically-unsaturated materials of most interest with regard to separation have 2 to about 8 carbon atoms, preferably 2 to 4 carbon atoms. The separation of aliphatically-unsaturated materials from admixtures containing other gaseous materials, such as the separation of ethylene or propylene from admixtures with other normally gaseous materials, e.g., one or more of ethane, propane, methane and hydrogen, is of particular importance. Frequently, such feed mixtures for the process contain about 1 to 50 weight percent ethylene, about 0 to 50 weight percent ethane and about 0 to 50 percent methane. Another process that may be of special significance is the separation from ethylene of minor amounts of acetylene.

The partial pressure of the material in the feed to be separated is at the input side of the liquid barrier used in the separation, greater than the partial pressure of this component on the discharge or exit side of the liquid barrier-semi-permeable membrane composite. This pressure drop across the membrane of the material to be separated may often be at least about 0.5 pound per square inch, and is preferably at least about 20 psi, although the pressure drop should not be so great that the liquid barrier is ruptured or otherwise deleteriously affected to a significant extent. Conveniently, the total pressure of the feed is up to about 1000 pounds per square inch. The partial pressure of the separated material upon discharge from the membrane can preferably be controlled by subjecting the exit side of the liquid barrier to the action of a sweep gas that may be essentially inert to forming a complex with the metal ions in solution in the liquid barrier. The sweep gas picks up the discharged or separated components of the feed, and the sweep gas may be selected so that it can be readily separated from the discharged components if that be necessary for the subsequent use of the latter. Unless a reaction with the separated material is desired, the sweep gas should be relatively inert therewith and may be, for instance, butane, carbon dioxide or the like.

The temperature across the liquid barrier-semi-permeable membrane composite employed in the separation procedure can be essentially constant or it may vary, and decomposition of the metal complex can be effected primarily by the drop in partial pressure of the material to be separated on the exit side of the liquid barrier compared with its partial pressure on the feed side. Conveniently, the temperature of the liquid barrier may be essentially ambient, especially in the case of feedstocks that are gaseous at this temperature and the pressure employed on the feed side of the liquid barrier. The temperature of the liquid barrier may, however, be reduced or elevated from ambient temperature. Often, the temperature may be up to about 100° C., and elevated temperatures may even be desired to put the feedstock in the gaseous or vapor phase. Neither the temperature nor the pressure used should, however, be such as to destroy the difference in transport rate across the liquid barrier, semi-permeable film composite, of the material whose separation is sought, compared with that of the other components of the feed. The conditions should also not be such that physical disruption of the liquid barrier or any other significant malfunction results.

The materials which can be employed to make the semi-permeable film membranes of the present invention may be of the hydrophilic types that have been heretofore employed for the separation or purification of various chemical materials. Among these hydrophilic film-forming materials are those disclosed in U.S. Pat. Nos. 3,228,877 and 3,566,580, incorporated herein by reference. Most advantageously, however, the materials employed may have a film-forming N-alkoxyalkyl polyamide as an essential component. The polyamide film-forming materials are generally known and have also been designated as nylons. The polymers are characterized by having a plurality of amide groups serving as recurring linkages between carbon chains in the product structure, and the polymers may be made by several procedures. Commonly, the polyamides are formed by reacting a polyamine and a dicarboxylic acid or its derivative such as an ester, especially a lower alkyl ester having, for instance, about 1 to 4 carbon atoms in the ester group. Other reactions which may be employed to form the polyamides include the self-condensation of monoamino, monocarboxylic acids and the reactions of cyclic lactams. In any event, the polyamide products contain recurring amide groups as an integral part of the principle polymer chain. The polyamides are described, for instance, in the Kirk-Othmer, *Encyclopedia of Chemical Technology*, Second Edition, Volume 16, beginning at page 1, Interscience Publishers, New York, 1968. Among the typical structural formulas of the linear polyamides are $H_2NRNH (COR'CONHRNH)_n COR'COOH$ and $H_2NRCO (NHRCO)_n NHRCOOH$, where R and R' represent primarily carbon-to-carbon chains between functional groups in the reactants, and n represents the degree of polymerization or the number of recurring groups in the polymer chain. The polyamides which can be used in this invention are generally solid at room temperature, and have a molecular weight which makes them suitable for forming the desired membranes.

The carboxylic acids which may be used in forming the polyamides have an acyloxy group (—R—COO—) in their structure and the R member of this group is composed essentially of carbon and hydrogen and often contains about 6 to 12 carbon atoms. Such groups may be aliphatic, including cycloaliphatic, aromatic, or a mixed structure of such types, but such groups are preferably aliphatic and saturated with respect to carbon-to-carbon linkages. These R groups may preferably have straight chain carbon-to-carbon or normal structures. Among the useful dicarboxylic acid reactants are adipic acid, sebacic acid, azelaic acid, isophthalic acid, terephthalic acid, and the methyl esters of these acids.

The polyamines employed in making the polyamides generally have at least two non-tertiary, amino nitrogen atoms. These nitrogen atoms may be primary or secondary in configuration, although amines having at least two primary nitrogen atoms are preferred. The polyamides may also have both primary and secondary nitrogen atoms and the polyamines may contain tertiary nitrogen atoms. The preferred polyamine reactants have aliphatic, including cycloaliphatic, structures, and often have from 2 to about 12 carbon atoms. Also, the preferred polyamines are saturated and have straight-chain structures, although branched-chain polyamines can be used. Among the useful polyamines are ethylene diamine, pentamethylene diamine, hexamethylene diamine, diethylene triamine, decamethylene diamine and their N-alkyl substituted derivatives, for instance, the lower alkyl derivatives which may have, for instance, 1 to 4 carbon atoms in the alkyl substituents.

The polyamide polymers which can be employed with particular advantage in this invention include those in which the film-forming polyamide is an N-alkoxyalkyl-substituted polyamide. Materials of this type are well known, as shown, for instance, by U.S. Pat. Nos. 2,430,910 and 2,430,923, which disclose N-alkoxymethyl polyamides made by the reaction of a polyamide polymer, formaldehyde and alcohol. Generally, at least about 5% of the amide groups of the polymer are substituted with alkoxyalkyl groups and such substitution may be up to about 60% or more. Preferably, this substitution is about 10 to 50% with the product being soluble in hot ethanol.

The alcohols employed in making the N-alkoxyalkyl polyamides are generally monohydric and may have, for instance, from 1 to about 18 or more carbon atoms. The lower alkanols are preferred reactants, especially the lower alkanols having 1 to 4 carbon atoms. Among the useful alcohols are methanol, propanols, butanols, oleyl alcohol, benzyl alcohol, lauryl alcohol and alcohol ethers, for instance, the alkyl ethers of ethylene glycol.

The N-alkyloxyalkyl polyamides which can be employed in the present invention to provide a desired semi-permeable membrane may be reacted with cross-linking agents. The cross-linking agents may be, for example, polycarboxylic acids, especially the dicarboxylic and tricarboxylic acids which may have, for instance, from 2 to about 12 carbon atoms. Useful acids include oxalic acid, citric acid, maleic acid, and the like.

Film-forming membranes which can advantageously be employed in the present invention can be made by intimately combining, by either physical means or through chemical reaction, the N-alkoxyalkyl polyamide and a hygroscopic polymer material, e.g., the water-soluble polyvinyl alcohols. The polyamides and hygroscopic polymer may be used as a physical admixture or in various reacted forms, for instance, as cross-linked polymers or block or graft copolymers. The hygroscopic polymer is generally employed in an amount sufficient to enhance the hydrophilic properties of the polyamide and may be up to about 75 weight % or somewhat more of the membrane composition based on the total polyamide and hygroscopic polymer, and the latter is often at least about 5 or 15% and the amount is sufficient to impart a significant property to the film-forming combination. Preferably, each of the hygroscopic polymer and the polyamide are about 25 to 75% of their combination or total amount, or the hydroscopic polymer may be about 35 to 55% and the polyamide about 45 to 65% of their combination.

The polyvinyl alcohols which can be employed in the membranes used in the present invention are essentially water-soluble materials, at least in hot water, and many of these are commercially available. The molecular weights of these polymers are often at least about 1000, and are commonly in the range of about 10,000 to 300,000. Suitable polyvinyl alcohols are described in, for example, "Water-Soluble Resins," Second Edition, Edited by Robert L. Davidson and Marshall Sittig, pages 109 to 115, Reinhold Book Corporation, New York, New York. The polyvinyl alcohol may be cross-linked, especially after membranes are formed from the polymeric materials. The presence of the cross-linked polyvinyl alcohol may increase the strength of the fibers or other membranes and increase their resistance to loss of polyvinyl alcohol by leaching during use. The polyvinyl alcohol may also be cross-linked by reaction with formaldehyde, e.g., by immersing the fibers in an aqueous bath containing 40% $(NH_4)_2SO_4$ and 10% HCHO and $7\frac{1}{2}\%$ $H_2SO_4$, at 50° C. for 1 to 3 hours.

The film membranes of this invention may advantageously be made from a mixture containing nylon, polyvinyl alcohol, di (lower alkyl) sulfoxide, and water as more fully described in copending U.S. patent application Ser. No. 419,091 filed on Nov. 26, 1973, and incorporated herein by reference.

The film membranes which can be employed in this invention are preferably self-supporting and have sufficient strength not to require any additional supporting material on either of its sides during use. With some films, however, it may be necessary, advantageous or convenient to provide adequate support such as additional film or sheet-like materials on one or both sides of the film membrane. These supporting structures are frequently very thin materials and may be permeable to both liquids and gases and not serve a separating function with respect to any component of the feed stream. Alternatively, the supporting film may be permeable to gases, but not to liquids.

The film membranes may be in the form of flat disc-like films, for example, or may be extruded membranes in the form of thin hollow fibers. In flat form the film membranes may have a thickness of up to about 30 mils or more. Preferably the thickness is up to about 10 or 15 mils. The films are sufficiently thick to avoid rupture during use and generally have a thickness of at least about 0.05 mil. In one preferred embodiment the membranes are formed by extrusion into thin walled fibers.

A suitable process for extruding the fibers involves providing the mixture having an elevated temperature suitable for extrusion, for instance, a temperature of about 60° to 125° C., preferably about 70° to 110° C. The material is extruded to form fibers having a hollow core surrounded by the membrane wall. During extrusion it is advantageous to pass a gas through the core of the hollow fibers to help cool the fibers and prevent the core of the fibers from closing. After extrusion the fibers can be dried to remove solvents and other low boiling materials. The resulting membranes have sufficient thickness so as not to be readily ruptured or otherwise undergo physical deterioration at a rate that would make their use unattractive. Generally the thickness of the fiber wall may be up to about 30 mils or more, preferably about 0.5 to 15 mils, and often the thickness is at least about 0.1 mil. The overall diameter of the fiber may usually be up to about 75 mils, preferably about 1 to 30 mils.

The properties, for instance, the strength and permeability, of the membrane fibers may be improved by drawing or stretching them and this can be accomplished at ambient or elevated temperatures. Suitable elevated temperatures include about 90° to 300° C., preferably about 125° to 200° C. The fibers may also be annealed at such temperatures, and the stretching and annealing may be accomplished simultaneously. The drawn fibers have a reduced overall diameter and thinner walls than before stretching whether at ambient or elevated temperature, and this treatment may preferably increase the length of the fibers by a factor of at least about 1.25, say up to about 10 or more. This treatment may decrease the thickness of the walls to where they are less than about 0.5 of the thickness they had before stretching. Excessive stretching may adversely affect the strength and performance of the fibers and thus we prefer that their length may not be increased by a factor of more than about 9. The stretching of the fibers is preferably accomplished when they are swollen with an aqueous or organic liquid. The swelling agent is preferably water. The amount of swelling agent present during stretching is often a minor amount up to about 50 weight percent of the fiber, preferably is at least about 1 weight percent.

In the present invention, the metals in the film or in the liquid barrier solution, which metals may serve in the form of metal-containing cations to separate a component from a mixture through the formation of metal complexes of desired properties, include, for instance, the transition metals of the Periodic Chart of Elements having atomic numbers about 20. Included in these metals are those of the first transition series having atomic numbers from 21 to 29, such as chromium, copper, especially the cuprous ion, manganese and the iron group metals, e.g., nickel and iron. Others of the useful complex-forming metals are in the second and third transition series, i.e., having atomic numbers from 39 to 47 or 57 to 79, as well as mercury, particularly as the mercurous ion. Thus, we may employ noble metals such as silver, gold and the platinum group, among which are platinum, palladium, rhodium, ruthenium and osmium. The useful base metals of the second and third transition series include, for example, molybdenum, tungsten, rhenium and the like. Various combinations of these complex-forming metals may also be employed in this invention, either in the presence or absence of other non-metal or non-complexing metal components.

The metal is provided in the film or in the aqueous liquid barrier of the separation system in a form which is soluble in this liquid. Thus, the various water-soluble salts of these metals can be used such as the nitrates and halides, for instance, the bromides and chlorides, fluoborates, fluosilicates, acetates, carbonyl halides or other salts of these metals which can serve to form the desired water-soluble complexes when the film is in contact with water. The metal salts should not react with any components of the chemical feedstock used in the separation procedure to form an insoluble material which could block the film membrane or otherwise prevent the separation of a component from the feedstock. Also, in a given system, the metal is selected so that the complex will readily form, and yet be sufficiently unstable, so that the complex will decompose and the dissociated material leave the liquid barrier, thereby providing a greater concentration of the material to be separated from the exit side of the membrane than is in the feed. The concentration of the metal ions in the film or liquid barrier may be rather low and still be sufficient to provide an adequate complexing rate so that excessive amounts of the semi-permeable membrane surface will not be needed to perform the desired separation. Conveniently, the concentration of the complex-forming metal ions in the aqueous solution forming the liquid barrier is at least about 0.1 molar and is preferably about 0.5 to 12 molar. Advantageously, the solution is less than saturated with respect to the complex-forming metal ions to insure that essentially all of the metal stays in solution, thereby avoiding any tendency to plug the film membrane and destroy its permeability characteristics.

When the complexing ions in the liquid barrier employed in this invention include cuprous ions, ammonium ions can be used to provide copper ammonium complex ions which are active to form a complex with the material to be separated by the use of the film. We preferably supply about equimolar amounts of cuprous and ammonium ions, although either type of ions may be in excess. The ammonium ions can be provided in various convenient ways, preferably as an acid salt such as ammonium chloride or as ammonium hydroxide or ammonium carbonate. In order to enhance the selectivity of the copper ammonium ion complex in the separation of this invention, we may also make the film and thus the liquid barrier solution more acidic, by, for instance, providing a water-soluble acid such as a mineral acid, especially hydrochloric acid in the film or liquid barrier solution. Preferably, the pH of the liquid barrier in this form of the invention is below about 5 with the acid in the solution. Since silver may form undesirable acetylides with acetylenes, the copper ammonium complex may be a more attractive complexing agent when it is desired to use the film to separate acetylenes from various mixtures.

Instead of supplying only a noble metal for complexing the material to be separated in the process of this invention, we may also employ mixtures of noble metal and other cation-providing materials. A portion of the noble metal may be replaced by non-noble metal or ammonium components. Accordingly, the total of such ion-forming materials in the film or in the liquid barrier may be composed of a minor or major amount of either the noble metal or the non-noble metal, ammonium or other components. Solutions having a major amount of the non-noble metal, ammonium or other cation-providing materials not containing a noble metal will generally be less expensive, and, accordingly, the noble metal may be as little as about 10 molar percent or less of the total cation-providing material in the solution. To reduce expenses, at least about 10 molar percent, preferably at least about 50 molar percent, on a cation basis of the total, of a cation-providing material may be other than noble metal. The non-noble or base metals are preferably of Groups II to VIII of the Periodic Chart of Elements, and especially those in the fourth and fifth periods, aluminum and magnesium. Zinc and copper ions are preferred ones among these non-noble or base metal components. The various metals may be provided in the liquid barrier in the form of any suitable compound, such as the acid salt forms mentioned above with respect to the noble metals.

In the system of the present invention, the amount of complex-forming metal in the semi-permeable membrane may vary considerably, but is sufficient to accomplish the desired separation. Often, this is a minor amount, say, about 1 to 50 weight percent, of the weight of the membrane on a non-aqueous basis, preferably about 5 to 25 weight percent. A suitable procedure for placing the solution of complex-forming metal in the semi-permeable film is by contacting the film with the solution and exerting a differential pressure across the solution and film. Thus, the pressure behind the solution is greater than that on the opposite side of the film, and as a result, the solution is forced into the film under pressure. Conveniently, the pressure of the solution is above atmospheric, and the opposite side of the film is essentially at atmospheric pressure. The pressure differential need not be large, for instance, it may only be at least about 5 or 10 psi, and it should not be so great that the film is ruptured.

This invention will be further illustrated by the following specific examples.

EXAMPLE I

Dry fibers having an inner diameter of 0.021 inches and an outer diameter of 0.033 inches and containing 30 wt. % polyvinyl alcohol (Borden's 0 to 0.5% acetate, average molecular weight of about 12,360 as determined by gel permeation), and 70 wt. % nylon (Belding, BCI-819, a methoxymethyl 6:6 nylon) are formed by extrusion from a mixture of 14.3 wt. % polyvinyl alcohol, 33.3 wt. % nylon, and 47.6 wt. % of a 4.8 wt. % water in dimethyl sulfoxide solvent solution. After extrusion, the fibers are dried at 75° C. for two hours, cross-linked at 50° C. for one hour in a bath containing 5% $Na_2SO_4$ and 3% p-toluene sulfonic acid, washed three times with distilled water and dried.

Ten of the fibers each having an effective length of about 11 inches, are bundled into an array using Dow Sylgard 184 potting agent at each end. This produces a total surface area of about 46.8 $cm^2$ based on the fiber inner diameter. In the separation unit the hollow fibers were arranged in an array within a glass tube. Feed gas containing the material to be separated entered one end of the inside of the hollow fibers and raffinate exited the other end of the fibers. The separated material passed from the inside of the hollow fibers to the outside and was removed from the vicinity of the fiber membranes by a sweep gas passing along the outside of the fibers.

In this example, the fibers are impregnated by soaking in aqueous 2 N $AgNO_3$ for fifteen minutes and then are rinsed with acetone and placed in the glass tube. A feed mixture containing 15.3% methane, 44.7% ethane, and 40.0% ethylene and having a relative humidity of about 50% is fed through the inside of the hollow fibers at a pressure of 20 psig and a flow rate of 10 ml./min. A relatively dry nitrogen purge or sweep gas at atmospheric pressure is passed through the glass tube around the outside of the hollow fibers at a rate of 10 ml./min.

In this example, no water is deposited on the outside of the fiber membranes after initial impregnation with silver nitrate solution and during five days of continuous operation the permeation rate drops from a start-up rate of $35 \times 10^{-4}$ ml./$cm^2$ min. down to $10 \times 10^{-4}$ ml./$cm^2$min. At the end of six days, the permeation rate is down to zero.

EXAMPLE II

The separation unit and procedure of Example I are again used, but the hollow fibers from Example I are reimpregnated with a 4 N $AgNO_3$ solution for thirty minutes. Gas feed and sweep gas conditions are the same as in Example I but both the feed and sweep gases have a relative humidity of about 100% instead of 50%. No water is deposited on the outside of the membranes. As in Example I, the permeation rate drops to about zero after six days of continuous operation.

EXAMPLE III

The separation unit and procedure of Example I are again used and the fibers from Example II exhibiting a permeation rate of about zero are first soaked in distilled water for two minutes and then employed in the separation process continuously until permeability again approaches zero. At this time an embodiment of the process of this invention is used. The temperature of the humidifier for the nitrogen purge gas is raised to 60° C. and the line between the humidifier and the inlet to the separation unit is heated to prevent condensation. As the purge gas reaches the fibers, which are at about 24° C., excess water condenses onto the outside of the fibers and causes the ethylene permeation rate to increase slowly. The performance levels are shown in Table 1 below. At the end of six days of continuous operation with water being deposited on the membrane the permeability has leveled off at about $25 \times 10^{-4}$ ml./$cm^2$min. and the percent ethylene in the product has leveled off at about 97.5%.

TABLE 1.

| Day of Continuous Operation | Permeability ml./$cm^2$ min. ($\times 10^{-4}$) | % Ethylene in Product |
|---|---|---|
| 1 | 11 2 | about 90 |
| 2 | 4 | about 92.5 |
| 3 | 7 | about 94.5 |
| 4 | 16 | 97.5 |
| 5 | 27 | 97.8 |
| 6 | 24 | 97.6 |
| 7 | — | 98.1 |
| 8 | — | 97.0 |

EXAMPLES IV–VI

As examples of different modes of operation of the invention, the following Examples IV–VI were performed:

Fibers were prepared from a polymer mixture containing 180 gms BCI-819 nylon (Belding Chemical Industries), 120 gms polyvinyl alcohol (DuPont's Elvanol 71-30), 270 ml dimethyl sulfoxide, and 30 ml water. The mixture was extruded through an annular die (O.D.=0.030" and I.D.=0.014"). The polymer was pumped through the outer portion at the rate of 12 ml/min while air was pumped through the inner part at the rate 0.38 ml/min. In this manner a fiber was produced which had an O.D. of 0.0237" and an I.D. of 0.0072".

During the extrusion, the fiber was quenched in an acetone bath for at least 30 min, and then air dried. The nylon polymer was cross-linked by immersing the fibers in a bath containing 3% p-toluene sulfonic acid and 5% $Na_2SO_4$ at 50° C. for 1 hour. Following this, the fibers wery washed three times in distilled water to remove any of the remaining cross-linking bath salts.

Next, the fibers were oriented by passing them through a 4-foot long tube furnace at 80° C. and at the rate of 3 feet/min. While they were passing through the furnace, they were stretched with a 200 gm weight. After this orientation they were annealed at 170° C. for 10 min while under no stress. The final fibers had an O.D. of 0.0215" and an I.D. of 0.0055".

Six 19" sections of this fiber were potted into a unit using Sylgard (Dow) 184 encapsulating agent. After the potting was completed 12" of active length for each fiber and a total fiber area for the unit of 18.4 cm² were obtained between potting joints.

This unit was tested under three different modes of operation, all with the feed on the outside of the fiber at 100 p.s.i.g. and at a flow of 2 ml/min and with a helium purge stream on the inside of the fiber at about atmospheric pressure and at a flow of 2 ml/min. For example IV, the shell side of the bundle was filled with a 6 N $AgNO_3+0.3\%$ $H_2O_2$ solution, and a 0.3% $H_2O_2$ solution was trickled through the length of the fibers at the rate of 0.0019 ml/min. For Example V, the shell side was filled with a 6 N $AgNO_3$-0.3% $H_2O_2$ solution, and a 4 N $AgNO_3+0.3\%$ $H_2O_2$ solution was trickled through the length of the fibers at the rate of 0.0016 ml/min. For Example VI, the shell side was free of solution and a 4 N $AgNO_3+0.3\%$ $H_2O_2$ solution was trickled through the length of the fibers at the rate of 0.0016 ml/min.

The results of this test and the number of days for each mode are given in accompanying Table 2. The results show that operation for all three modes is comparable and that good permeation rates may be maintained for many days of operation by maintaining the gas exit side of the membrane with a supply of water.

TABLE 2.

Comparison of Methods for Operating Membrane Unit
(Feed Pressure = 100 psig; Feed Rate = 2 ml/min; Purge Rate = 2 ml/min)

| Unit | No. of Days on Stream | Wt % $CH_4$ | Product Wt % $C_2H_4$ | Wt % $C_2H_6$ | Permeation Rate ml/cm² min |
|---|---|---|---|---|---|
| Feed | — | 20.59 | 40.13 | 39.28 | — |
| Example IV (6 N $AgNO_3$ + 0.3% $H_2O_2$ outside and 0.3% $H_2O_2$ inside) | 8 | 0.32 | 99.26 | 0.42 | .00208 |
| Example V (6 N $AgNO_3$ + 0.3% $H_2O_2$ outside and 4 N $AgNO_3$ + 0.3% $H_2O_2$ inside) | 7 | 0.40 | 98.99 | 0.61 | .00174 |
| Example VI (nothing outside and 4 N $AgNO_3$ + 0.3% $H_2O_2$ inside) | 9 | 0.34 | 99.17 | 0.49 | .00184 |

It is claimed:

1. In a process for separating an aliphatically-unsaturated hydrocarbon from a fluid mixture comprising contacting said mixture containing said aliphatically-unsaturated hydrocabon with a first side of an essentially solid, water-insoluble, hydrophilic semi-permeable membrane having therein an aqueous liquid barrier having metal-containing ions which combine with said aliphatically-unsaturated hydrocarbon to form a water-soluble complex, the partial pressure of said aliphatically-unsaturated hydrocarbon on a second side of the semi-permeable membrane being sufficiently less than the partial pressure of said aliphatically-unsaturated hydrocarbon in said mixture to provide the separated aliphatically-unsaturated hydrocarbon on the second side of the semi-permeable membrane, removing said separated aliphatically-unsaturated hydrocarbon from the vicinity of the second side of the semi-permeable membrane, the improvement comprising contacting the second side of the semi-permeable membrane with an aqueous, non-sweep liquid medium during said aliphatically-unsaturated hydrocarbon separation in an amount sufficient to reduce the loss of water from said aqueous liquid barrier during said separation.

2. The process of claim 1 wherein said fluid mixture is gaseous.

3. The process of claim 1 wherein the aliphatically-unsaturated hydrocarbon contains 2 to 4 carbon atoms.

4. The process of claim 3 wherein said separated aliphatically-unsaturated hydrocarbon is removed from the vicinity of the second side of the semi-permeable membrane by a substantially inert gas stream.

5. The process of claim 4 wherein the substantially inert gas stream is supersaturated and contact with the aqueous medium is achieved by condensation onto the second side of the semi-permeable membrane as the substantially inert gas stream removes said separate aliphatically-unsaturated hydrocarbon.

6. The process of claim 5 wherein the substantially inert gas stream is saturated at an elevated temperature and then cooled to supersaturation.

7. The process of claim 3 wherein the second side of the semi-permeable membrane is contacted with aqueous medium as a continuous liquid phase film during the separation process.

8. The process of claim 3 wherein said mixture is a mixture of ethylene and low molecular weight paraffins and said separated material is ethylene.

9. The process of claim 3 wherein said membrane comprises a polyamide membrane and said metal-containing ions are silver-containing ions.

10. The process of claim 9 wherein said polyamide is an N-methoxymethyl polyamide.

11. The process of claim 9 wherein said membrane further comprises polyvinyl alcohol.

12. The process of claim 11 wherein said membrane is comprised of hollow fibers.

13. The process of claim 9 wherein said membrane is comprised of hollow fibers.

14. The process of claim 13 wherein said polyamide is an N-methoxymethyl polyamide.

15. The process of claim 14 wherein said membrane further comprises polyvinyl alcohol.

16. The process of claim 14 wherein said mixture is a mixture of ethylene and low molecular weight paraffins and said separated material is ethylene.

17. The process of claim 13 wherein said second side of the semi-permeable membrane is the outside of said hollow fibers and it is contacted with aqueous medium as a continuous liquid phase film.

18. In a process for separating a material from a fluid mixture comprising contacting said mixture containing said material with a first side of an essentially solid, water-insoluble, hydrophilic semi-permeable membrane having therein an aqueous liquid barrier having metal-containing ions which combine with said material to form a water-soluble complex, the partial pressure of said material on a second side of the semi-permeable membrane being sufficiently less than the partial pressure of said material in said mixture to provide separated material on the second side of the semi-permeable membrane, removing said separated material from the vicinity of the second side of the semi-permeable membrane by a substantially inert gas stream, the improvement comprising contacting the second side of the semi-permeable membrane with an aqueous, non-sweep liquid medium during said material separation in an amount sufficient to reduce the loss of water from said aqueous liquid barrier during said separation.

19. In a process for separation a material from a fluid mixture comprising contacting said mixture containing said material with a first side of an essentially solid, water-insoluble, hydrophilic semi-permeable membrane having therein an aqueous liquid barrier having metal-containing ions which combine with said material to form a water-soluble complex, the partial pressure of said material on a second side of the semi-permeable membrane being sufficiently less than the partial pressure of said material in said mixture to provide separated material on the second side of the semi-permeable membrane, removing said separated material from the vicinity of the second side of the semi-permeable membrane with a sweep stream having less than a sweeping amount of aqueous liquid medium or with vacuum, the improvement comprising contacting the second side of the semi-permeable membrane with an aqueous, non-sweep liquid medium during said material separation in an amount sufficient to reduce the loss of water from said aqueous liquid barrier during said separation.

* * * * *

UNITED STATES PATENT OFFICE
CERTIFICATE OF CORRECTION

Patent No. 4,239,506                    Dated December 16, 1980

Inventor(s) Edward F. Steigelmann and Robert D. Hughes

It is certified that error appears in the above-identified patent and that said Letters Patent are hereby corrected as shown below:

Column 4, line 3, "copening" should be --copending--.

Column 5, line 51, "effecitve" should be --effective--.

Column 5, line 68, after the word "provide" the word "a" was omitted.

Column 6, line 18, "often" should be --Often--.

Column 7, line 28, after "50" second occurrence should read "weight".

Column 11, line 28, the word "about" should be --above--.

Column 14, about line 27, the first figure in the middle column, "11 2" should be --2--.

Column 14, line 57, "wery" should be --were--.

Column 15, Table 2, in the headings, the solid line beneath "Product" should extend above "Wt % $CH_4$".

UNITED STATES PATENT OFFICE
CERTIFICATE OF CORRECTION

Patent No. 4,239,506    Dated December 16, 1980

Inventor(s) Edward F. Steigelmann and Robert D. Hughes

It is certified that error appears in the above-identified patent and that said Letters Patent are hereby corrected as shown below:

Column 15, line 56, claim 1, "hydrocabon" should be --hydrocarbon--.

Column 16, line 22, claim 5, the word "separate" should be --separated--.

Signed and Sealed this

Twenty-first Day of April 1981

[SEAL]

Attest:

RENE D. TEGTMEYER

Attesting Officer    Acting Commissioner of Patents and Trademarks